United States Patent
Moss

(10) Patent No.: US 9,968,299 B2
(45) Date of Patent: May 15, 2018

(54) DEVICE, SYSTEM AND METHOD FOR COMMUNICATION WITH AN IMPLANTABLE MEDICAL DEVICE

(71) Applicant: BIOTRONIK SE & CO. KG, Berlin (DE)

(72) Inventor: Christian Moss, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 261 days.

(21) Appl. No.: 14/201,925

(22) Filed: Mar. 10, 2014

(65) Prior Publication Data

US 2015/0250406 A1  Sep. 10, 2015

(51) Int. Cl.
*A61B 5/00* (2006.01)
*A61N 1/372* (2006.01)

(52) U.S. Cl.
CPC .......... *A61B 5/6843* (2013.01); *A61B 5/0028* (2013.01); *A61B 5/0031* (2013.01); *A61B 5/6887* (2013.01); *A61N 1/37288* (2013.01); *A61B 2560/029* (2013.01); *A61B 2560/0468* (2013.01); *A61B 2562/0252* (2013.01); *A61N 1/37211* (2013.01)

(58) Field of Classification Search
CPC ... A61B 5/6843; A61B 5/0031; A61B 5/0028; A61B 5/6887; A61B 2562/0252; A61B 2560/0468; A61B 2560/029; A61N 1/37288; A61N 1/37211
See application file for complete search history.

(56) References Cited

U.S. PATENT DOCUMENTS

| | | | | |
|---|---|---|---|---|
| 4,987,897 A | * | 1/1991 | Funke | A61B 5/0028 607/32 |
| 5,113,859 A | | 3/1992 | Funke | |
| 6,076,016 A | | 6/2000 | Feierbach | |
| 6,115,636 A | * | 9/2000 | Ryan | A61N 1/37223 128/903 |
| 6,200,265 B1 | * | 3/2001 | Walsh | A61B 5/0031 128/903 |
| 8,109,874 B2 | * | 2/2012 | Kong | A61B 5/0205 128/920 |

(Continued)

FOREIGN PATENT DOCUMENTS

WO   WO 2013/126684 A1 * 8/2013 ........... A61B 5/7465

*Primary Examiner* — Meredith Weare
(74) *Attorney, Agent, or Firm* — Arc IP Law, PC; Joseph J. Mayo

(57) ABSTRACT

A device, system and method that communicate with at least one implantable medical device (IMD). The device includes a unit and a surface having at least one reception or transmission element that communicate with the at least one IMD. A minimum pressure required for the contact between transmission or reception elements and skin is provided by gravity or by patient interaction with the device. The system includes the at least one IMD, the unit that communicates with the at least one IMD and the device having the at least one reception or transmission element that communicate with the at least one IMD. The method includes the steps of providing a surface having at least one reception or transmission element that communicate with an IMD, and enabling communication upon detection of a minimum pressure on the surface. The communication with the IMD is acoustic or conductive.

18 Claims, 1 Drawing Sheet

(56) References Cited

U.S. PATENT DOCUMENTS

| | | | | |
|---|---|---|---|---|
| 8,626,295 | B2* | 1/2014 | Doron | G10K 9/122 |
| | | | | 607/32 |
| 8,644,915 | B2* | 2/2014 | Chou | A61B 5/0404 |
| | | | | 600/509 |
| 8,771,204 | B2* | 7/2014 | Telfort | A61B 5/6843 |
| | | | | 181/130 |
| 2004/0117212 | A1* | 6/2004 | Kong | G06Q 50/22 |
| | | | | 705/2 |
| 2010/0274099 | A1* | 10/2010 | Telfort | A61B 5/6843 |
| | | | | 600/300 |
| 2011/0218594 | A1* | 9/2011 | Doron | G10K 9/122 |
| | | | | 607/60 |
| 2012/0116240 | A1* | 5/2012 | Chou | A61B 5/0424 |
| | | | | 600/523 |
| 2015/0031964 | A1* | 1/2015 | Bly | A61B 5/165 |
| | | | | 600/301 |

* cited by examiner

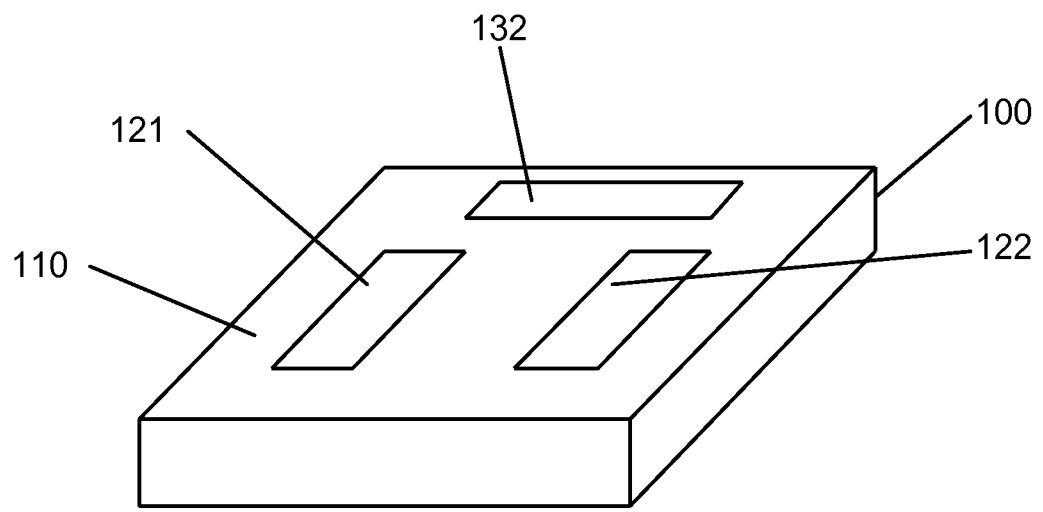

DEVICE, SYSTEM AND METHOD FOR COMMUNICATION WITH AN IMPLANTABLE MEDICAL DEVICE

BACKGROUND OF THE INVENTION

Field of the Invention

At least one embodiment of the invention relates to a device, a system and a method for communication with an implantable medical device.

Description of the Related Art

Typically, implantable medical devices (IMD) used for delivering a therapy or monitoring a physiologic condition of a human may collect and store various data such as diagnostic, therapy and device status data. Generally, to make the data available to a patient, a physician or a health care provider, such devices may include a telemetry unit to transmit these data to a device that is located externally of the body. The external device, generally, may be for example a patient device, a medical device programmer or a relay device that forwards the data to a remote server or database. Typically, to enable a data communication from an IMD to an external device, various technologies may be employed. Communication using radio frequency (RF) transmission and reception is most often used, as the external device may be in a distance up to several meters. The drawback of this technology, generally, is the high demand of energy for the communication. Typical alternatives with lower energy demand for communication often include techniques based on acoustic transmission or conductive connection using the body as conductor, which are particularly advantageous for IMD having limited energy, such as implantable sensors or in general small IMDs. The drawback of using such technologies, generally, is the need of a close contact between an external reception or transmission device and the patient's skin. For example, typically, to enable acoustic communication, a transducer needs to be placed with minimum pressure on the skin of the patient. Similarly, to enable conductive communication, typically, electrodes need to be placed with minimum pressure on the skin of the patient. Generally, this may complicate the use of the device, may limit the patient's comfort during use, and may also impact the acceptance of such technologies by the patients. An example for an acoustic communication unit is disclosed in U.S. Pat. No. 5,113,859. An example for a conductive communication unit is disclosed in U.S. Pat. No. 6,076,016.

Therefore, there is a need for an improved device, system and method for communication with an implantable medical device. Particularly, there is a need for a device, system and method for communication with an implantable medical device that improves patient comfort during use.

BRIEF SUMMARY OF THE INVENTION

In one or more embodiments of the invention, a device is provided that communicates with at least one implantable medical device (IMD). In at least one embodiment, the device may include a unit that communicates with the at least one IMD, and a surface having at least one reception or transmission element that communicates with the at least one IMD. According to one or more embodiments, minimum pressure is required for the contact between the transmission or reception elements and skin, which may be provided by gravity or patient interaction with the device. For example, in at least one embodiment, at least a part of the patient's body mass or a force of the patient provides the minimum pressure required for the contact between the transmission or reception element and the skin. In one or more embodiments, the pressure to the device is detected or measured, and is used to enable and/or control the communication.

By way of at least one embodiment, a system is provided and may include one or more of at least one IMD, a unit that communicates with the at least one IMD, and the device having the at least one reception or transmission element that communicates with the at least one IMD.

According to one or more embodiments of the invention, a method is provided that includes communicating with the at least one IMD, wherein the method may include one or more of the steps of providing a surface having at least one reception or transmission element for communication with an IMD, and enabling communication upon detection of a minimum pressure on the surface. In at least one embodiment, the communication with the IMD may be acoustic or conductive.

BRIEF DESCRIPTION OF THE DRAWINGS

The above and other aspects, features and advantages of at least one embodiment of the invention will be more apparent from the following more particular description thereof, presented in conjunction with the following drawings wherein:

FIG. 1 is an illustration of at least one embodiment of the invention.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

According to one or more embodiments of the invention, the at least one IMD may include one or more of an implantable therapy device, a monitoring device and a sensing device. In at least one embodiment, the at least one IMD senses and/or detects one or more of at least one physiological parameter of the body and a technical parameter of the device. In one or more embodiments, the at least one IMD may include a communication unit that sends at least one of the at least one physiological parameter and the technical parameter of the device to an external device. In at least one embodiment, the communication unit of the at least one IMD may include acoustic and/or conductive communication.

In one or more embodiments, acoustic communication includes the contact of at least one acoustic transducer to a patient's skin.

By way of at least one embodiment, the contact may be indirect, using an adaptation material between the at least one acoustic transducer and the patient's skin to improve the propagation of the acoustic waves. Depending on the direction of communication, in at least one embodiment, the at least one acoustic transducer may act as at least one transmission or reception element.

In one or more embodiments of the invention, conductive communication includes the contact of at least two conducting electrodes to the patient's skin. The at least two conducting electrodes, in at least one embodiment, may include conducting material having a resistance between zero and at least one hundred ohms. In one or more embodiments, the at least two conducting electrodes may also act as at least one transmission or reception element.

By way of at least one embodiment, the at least one transmission and/or reception element may be integrated in or be part of a device in various ways as described hereafter. In one or more embodiments, the device may include at least one of the transmission or reception elements and/or a unit that determines the pressure to the at least one transmission or reception element. The device, in at least one embodiment, may include or may be connected to a unit that communicates with the at least one IMD. In one or more embodiments, data received by the communication unit may be one or more of stored, displayed and forwarded to a further remote device. The device, in at least one embodiment, may optionally include one or more of a second communication interface that communicates with one or more of a remote device, a memory and a display. One or more embodiments of the invention determine the mass of the patient, wherein this mass may be one or more of stored, displayed and forwarded to a further remote device. In one or more embodiments of the invention, the patient may establish a bare skin contact with one or more of the at least one transmission or reception elements.

FIG. 1 illustrates at least one embodiment of the invention. In at least one embodiment of FIG. 1, the device 100 may be integrated in or be part of a person's at least one measurement scale as shown. In one or more embodiments, at least one transmission and/or reception element 121, 122 may be located at or may be in the upper horizontal surface 110 of the at least one measurement scale, such that feet of the patient stand on the at least one transmission and/or reception element. In at least one embodiment, the at least one transmission and/or reception elements 121, 122 may be connected to a unit that communicates with the at least one IMD. In one or more embodiments, data received by the communication unit may be one or more of stored in an optional memory, displayed on an optional human interface 132 that is connected to or part of the device 100, and forwarded using a second communication interface to a further remote device. In at least one embodiment, the human interface 132 may be selected from various interfaces, such as alphanumerical and/or graphical displays, input devices or any combinations thereof. In one or more embodiments, the human interface 132 may display one or more of the mass of the patient, status information regarding communication and instructions.

For example, in at least one embodiment of the invention, the status information may include, but is not limited to, information about the quality of communication or the progress of communication, and/or any other status information. In one or more embodiments, the instructions may include, but is not limited to, one or more of instructions to change feet position in case the communication quality is poor, instructions to remain in the position until the communication is finished, and the like.

By way of at least one embodiment, the device 100 may include a sensor (not shown in FIG. 1) that detects at least whether a minimum force to the horizontal surface 110 is exceeded. Alternatively, in at least one embodiment, a mass sensor may be used to determine the mass of the patient.

In at least one embodiment of the invention with acoustic communication, at least one transmission and/or reception element may be located at or in the upper horizontal surface of the at least one measurement scale, such that the bare feet of the patient stand on the at least one transmission and/or reception element. In one or more embodiments, the pressure to the at least one transmission and/or reception element is determined by measuring the force to the horizontal surface and/or by measuring the mass of the patient. If one or more of the force to the horizontal surface or the mass of the patient exceed a minimum threshold equivalent to the minimum pressure required for communication, in at least one embodiment, the communication is activated.

In at least one embodiment of the invention with conductive communication, at least two transmission and/or reception elements may be located at or in the upper horizontal surface of the at least one measurement scale, such that each of the bare feet of the patient stand on the at least one of the transmission and/or reception elements. In one or more embodiments, the pressure to the at least one transmission and/or reception element may be determined as described above regarding acoustic communication. Alternatively, in one or more embodiments, the skin resistance between the electrodes is measured, and if the resistance exceeds a minimum threshold required for communication, the communication is activated.

In at least one embodiment of the invention, the device may be integrated in or be part of a toilet seat. In one or more embodiments, at least one transmission and/or reception element may be located at or in the upper horizontal surface of the toilet seat, such that the patient sits on the at least one transmission and/or reception element. In at least one embodiment, the toilet seat may include a sensor that detects at least whether a minimum force to the horizontal surface of the seat is exceeded. Alternatively, in at least one embodiment, a mass sensor may be used. The activation of the communication, in one or more embodiments, is activated as discussed above.

In at least one embodiment of the invention with conductive communication, at least two transmission and/or reception elements may be isolated from each other and may be located at or in the upper part of the surface of a horizontal bar. In one or more embodiments, the horizontal bar may include a sensor that detects at least whether a minimum force to the horizontal bar is exceeded. Alternatively, in at least one embodiment, a mass sensor may be used. The activation of the communication, in at least one embodiment, is activated as discussed above.

In at least one embodiment of the invention with conductive communication, at least two transmission and/or reception elements may be isolated from each other and may be part of one or more handles of a fitness device. The fitness device, in one or more embodiments, may include a sensor that detects the exceeding of a minimum force to the one or more handles. The activation of the communication, in at least one embodiment, is activated as discussed above.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A communication device configured to communicate with at least one implantable medical device (IMD) implanted in a patient, the communication device comprising:
   a surface configured to communicate with the at least one IMD via acoustic communication, and to contact skin of the patient, the surface comprising:
   a user interface, at least one reception or transmission element configured to be integrated in or part of the surface, wherein said at least one reception or transmission element comprises at least one acoustic transducer configured to contact the skin of the patient, such that said surface is configured to contact the skin of the patient via said acoustic transducer,
a force sensor configured to measure a force to said surface, and
a mass sensor configured to measure a mass of said patient,
wherein said communication device is configured to determine a contact pressure provided between said surface and the skin of the patient by gravity or by patient interaction with the communication device by measuring the force to said surface from said force sensor and by measuring the mass of the patient from said mass sensor,
wherein said communication device is further configured to use said contact pressure to one or more of enable and control communication with said at least one IMD by activating said acoustic communication when the force to the surface and the mass of the patient exceed a minimum threshold equivalent to a minimum pressure required for contact between the at least one reception or transmission element and the skin of the patient to communicate with said at least one IMD, and
wherein said user interface displays one or more of said mass of the patient, status information regarding said communication, and instructions.

2. The communication device according to claim 1, wherein
said surface is further configured to communicate with the at least one IMD via conductive communication,
said at least one reception or transmission element further comprises at least two conducting electrodes configured to contact the skin of the patient such that said surface is configured to contact the skin of the patient via said at least two conducting electrodes,
said communication device is further configured to determine contact pressure between said at least two conducting electrodes and the skin of the patient by measuring a skin resistance between said at least two conducting electrodes, and
the communication device is further configured to activate the conductive communication when the skin resistance exceeds a minimum threshold equivalent to a minimum pressure required to communicate between the communication device and the at least one IMD.

3. The communication device according to claim 1, wherein said user interface comprises one or more of alpha-numerical displays, graphical displays and input devices.

4. The communication device according to claim 1, wherein said status information comprises information about one or more of a quality of said communication and a progress of said communication, and wherein said instructions comprise one or more of instructions to change a position in case said quality of said communication is poor and instructions to remain in a position until said communication is finished.

5. The communication device according to claim 1, wherein
said communication device is further configured to be integrated in or be part of said patient's at least one measurement scale,
said surface is a surface of said at least one measurement scale,
said at least one reception or transmission element is located at or is in said surface of said at least one measurement scale, such that said at least one reception or transmission element is configured to enable feet of said patient to stand on said at least one reception or transmission element, and
via said feet of the patient on the at least one reception or transmission element, said contact pressure to the at least one reception or transmission element is determined by measuring the force to said surface of said at least one measurement scale and measuring the mass of the patient.

6. The communication device according to claim 1, wherein the communication device is further configured to be integrated in or be part of a toilet seat, wherein said surface is a surface of said toilet seat, and wherein the at least one reception or transmission element is located at or in said surface of the toilet seat, such that said at least one reception or transmission element is configured to enable said patient to sit on the at least one reception or transmission element.

7. A system comprising:
at least one implantable medical device (IMD) configured to be implanted in a patient; and
a communication device configured to communicate with the at least one IMD, the communication device comprising:
a surface configured to communicate with the at least one IMD via acoustic communication, and to contact skin of the patient, the surface comprising:
a user interface,
at least one reception or transmission element configured to be integrated in or part of the surface, wherein said at least one reception or transmission element comprises at least one acoustic transducer configured to contact the skin of the patient, such that said surface is configured to contact the skin of the patient via said acoustic transducer,
a force sensor configured to measure a force to said surface, and
a mass sensor configured to measure a mass of said patient,
wherein said communication device is configured to determine a contact pressure provided between said surface and the skin of the patient by gravity or by patient interaction with the communication device by measuring the force to said surface from said force sensor and by measuring the mass of the patient from said mass sensor,
wherein said communication device is further configured to use said contact pressure to one or more of enable and control communication with said at least one IMD by activating said acoustic communication when the force to the surface and the mass of the patient exceed a minimum threshold equivalent to a minimum pressure required for contact between the at least one reception or transmission element and the skin of the patient to communicate with said at least one IMD, and
wherein said user interface displays one or more of said mass of the patient, status information regarding said communication, and instructions.

8. The system according to claim 2, wherein
said surface is further configured to communicate with the at least one IMD via conductive communication,
said at least one reception or transmission element further comprises at least two conducting electrodes configured to contact the skin of the patient such that said surface is configured to contact the skin of the patient via said at least two conducting electrodes, wherein said communication device is further configured to determine a contact pressure between said at least two conducting electrodes and the skin of the patient by measuring a skin resistance between said at least two conducting electrodes, and wherein the communication device is further configured to activate the conductive communication when the skin resistance exceeds a minimum threshold equivalent to a minimum pressure required to communicate between the communication device and the at least one IMD.

9. The system according to claim 7, wherein said user interface comprises one or more of alphanumerical displays, graphical displays and input devices.

10. The system according to claim 7, wherein said status information comprises information about one or more of a quality of said communication and a progress of said communication, and wherein said instructions comprise one or more of instructions to change a position in case said quality of said communication is poor and instructions to remain in a position until said communication is finished.

11. The system according to claim 7, wherein said communication device is further configured to be integrated in or be part of said patient's at least one measurement scale, said surface is a surface of said at least one measurement scale, said at least one reception or transmission element is located at or is in said surface of said at least one measurement scale, such that said at least one reception or transmission element is configured to enable feet of said patient to stand on said at least one reception or transmission element, and via said feet of the patient on the at least one reception or transmission element, said contact pressure to the at least one reception or transmission element is determined by measuring the force to said surface of said at least one measurement scale and measuring the mass of the patient.

12. The system according to claim 7, wherein the communication device is further configured to be integrated in or be part of a toilet seat, wherein said surface is a surface of said toilet seat, and wherein the at least one reception or transmission element is located at or in said surface of the toilet seat, such that said at least one reception or transmission element is configured to enable said patient to sit on the at least one reception or transmission element.

13. A method of communicating with at least one implantable medical device (IMD) comprising the steps of:

providing a communication device comprising:

a surface configured to communicate with the at least one IMD via acoustic communication, and to contact skin of the patient, the surface comprising:

a user interface, at least one reception or transmission element configured to be integrated in or part of the surface, wherein said at least one reception or transmission element comprises at least one acoustic transducer configured to contact the skin of the patient, such that said surface is configured to contact the skin of the patient via said acoustic transducer, a force sensor configured to measure a force to said surface, and a mass sensor configured to measure a mass of said patient, providing contact between said surface and the skin of the patient, determining a contact pressure provided between said surface and the skin of the patient by gravity or by patient interaction with the communication device surface by measuring the force to said surface from said force sensor and by measuring the mass of the patient from said mass sensor, using said contact pressure to one or more of enable and control communication with said at least one IMD by activating said acoustic communication when the determined contact pressure exceeds a minimum threshold equivalent to a minimum pressure required to communicate with said at least one IMD, and displaying, with said user interface, one or more of said mass of the patient, status information regarding said acoustic communication, and instructions.

14. The method according to claim 13, wherein said surface is further configured to communicate with the at least one IMD via conductive communication, said at least one reception or transmission element further comprises at least two conducting electrodes configured to contact the skin of the patient such that said surface is configured to contact the skin of the patient via said at least two conducting electrodes, the method further comprises determining a contact pressure between said at least two conducting electrodes and the skin of the patient by measuring a skin resistance between said at least two conducting electrodes, and activating the conductive communication when the skin resistance exceeds a minimum threshold equivalent to a minimum pressure required to communicate with the at least one IMD.

15. The method according to claim 13, wherein said user interface comprises one or more of alphanumerical displays, graphical displays and input devices.

16. The method according to claim 13, wherein said status information comprises information about one or more of a quality of said communication and a progress of said communication, and wherein said instructions comprise one or more of instructions to change a position in case said quality of said communication is poor and instructions to remain in a position until said communication is finished.

17. The method according to claim 13, wherein said communication device is further configured to be integrated in or be part of said patient's at least one measurement scale, said surface is a surface of said at least one measurement scale, said at least one reception or transmission element is located at or is in said surface of said at least one measurement scale, such that said at least one reception or transmission element is configured to enable feet of said patient to stand on said at least one reception or transmission element, and via said feet of the patient on the at least one reception or transmission element, said contact pressure to the at least one reception or transmission element is determined by measuring the force to said surface of said at least one measurement scale and measuring the mass of the patient.

18. The method according to claim 13, wherein the communication device is further configured to be integrated in or be part of a toilet seat, wherein said surface is a surface of said toilet seat, and wherein the at least one reception or transmission element is located at or in said surface of the toilet seat, such that said at least one reception or transmission element is configured to enable said patient to sit on the at least one reception or transmission element.

* * * * *